(12) United States Patent
Ross

(10) Patent No.: US 10,924,712 B2
(45) Date of Patent: Feb. 16, 2021

(54) TRAUMA SCENE MONITORING SYSTEM

(71) Applicant: First-Light USA, LLC, Seymour, IL (US)

(72) Inventor: Jeremy B. Ross, Monticello, IL (US)

(73) Assignee: First-Light USA, LLC, Seymour, IL (US)

( * ) Notice: Subject to any disclaimer, the term of this patent is extended or adjusted under 35 U.S.C. 154(b) by 0 days.

(21) Appl. No.: 15/929,465

(22) Filed: May 4, 2020

(65) Prior Publication Data

US 2020/0358987 A1 Nov. 12, 2020

Related U.S. Application Data

(60) Provisional application No. 62/845,444, filed on May 9, 2019.

(51) Int. Cl.

| | |
|---|---|
| *H04N 7/18* | (2006.01) |
| *A61B 5/00* | (2006.01) |
| *H04R 1/08* | (2006.01) |
| *H04R 1/10* | (2006.01) |
| *H04N 5/225* | (2006.01) |
| *A61B 90/35* | (2016.01) |
| *A61B 90/00* | (2016.01) |

(52) U.S. Cl.
CPC ........... *H04N 7/185* (2013.01); *A61B 5/0022* (2013.01); *A61B 5/747* (2013.01); *A61B 90/35* (2016.02); *A61B 90/361* (2016.02); *H04N 5/2253* (2013.01); *H04N 5/2256* (2013.01); *H04R 1/08* (2013.01); *H04R 1/1008* (2013.01); *A61B 2505/01* (2013.01); *H04R 2460/13* (2013.01)

(58) Field of Classification Search
None
See application file for complete search history.

(56) References Cited

U.S. PATENT DOCUMENTS

| | | | | |
|---|---|---|---|---|
| 10,496,788 | B2* | 12/2019 | Amarasingham | G16H 50/30 |
| 10,539,787 | B2* | 1/2020 | Haddick | G02B 27/0093 |
| 2009/0275808 | A1* | 11/2009 | DiMaio | A61B 6/04 |
| | | | | 600/301 |

\* cited by examiner

*Primary Examiner* — Christopher Braniff
(74) *Attorney, Agent, or Firm* — Ascenda Law Group, PC

(57) ABSTRACT

A trauma scene monitoring system includes a medic-worn illumination device, a casualty-worn informatics system, and a remote monitoring station. The illumination device includes a frame with boom-mounted light sources positioned below the wearer's eyes near the zygomatic bones, thus orienting the light sources to project light in the direction of the wearer's view. Also included are audio/video means to capture audio/video information from a scene attended by the medic, and a telemetry unit to transmit that information to the remote monitoring station. The casualty-worn informatics system is integrated within a headband worn by a monitored individual. The informatics system includes sensors to provide the monitored individual's vital statistics and a telemetry unit to transmit data concerning the monitored individual to the remote monitoring station. At the remote monitoring station, receiving and presentation stations provide views of the data concerning the monitored individual and audio/video data from the medic-worn illumination device.

10 Claims, 12 Drawing Sheets

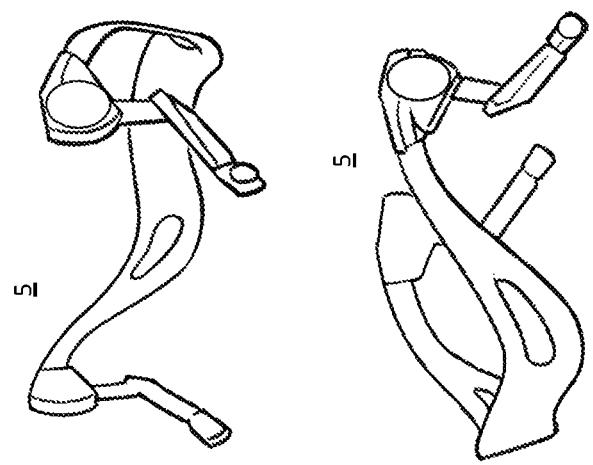
FIG. 4

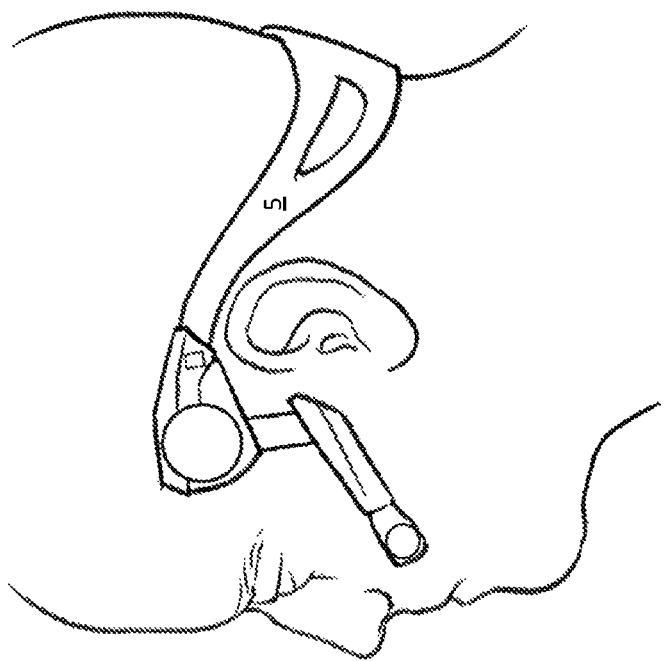
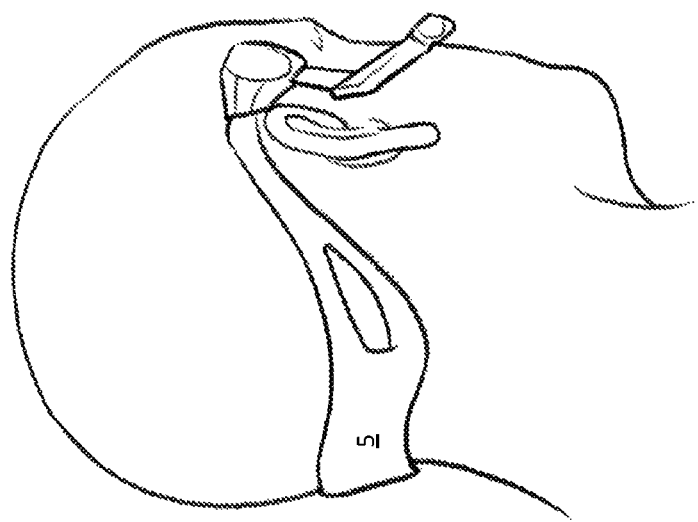
FIG. 5

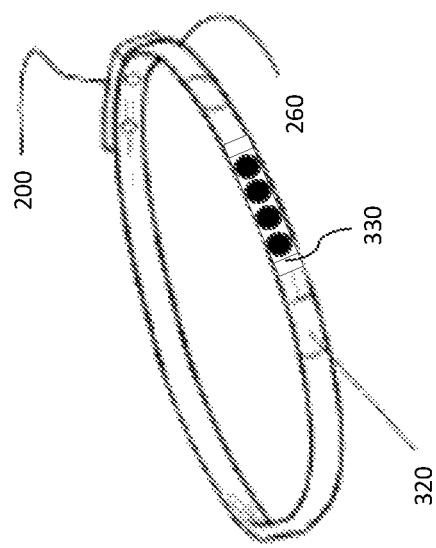
FIG. 13
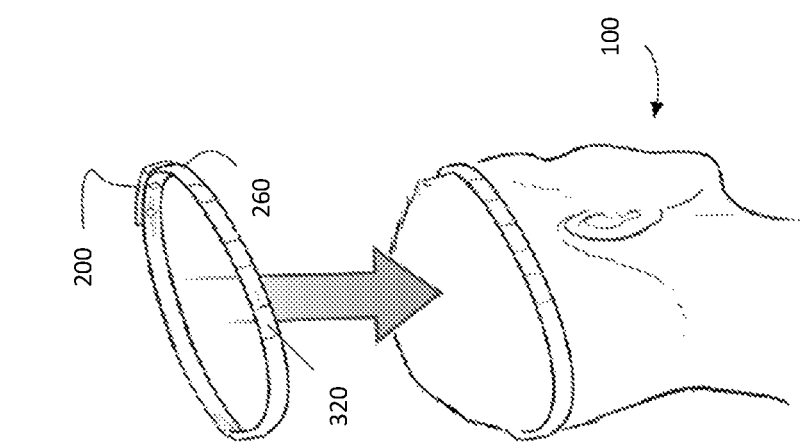
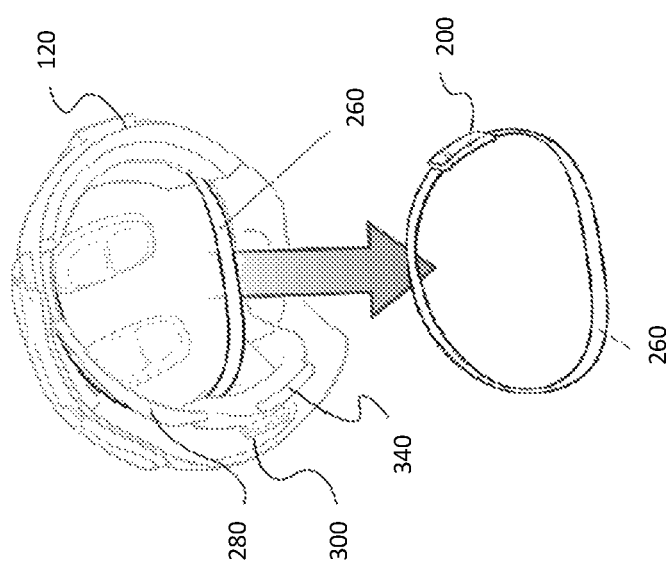
FIG. 10

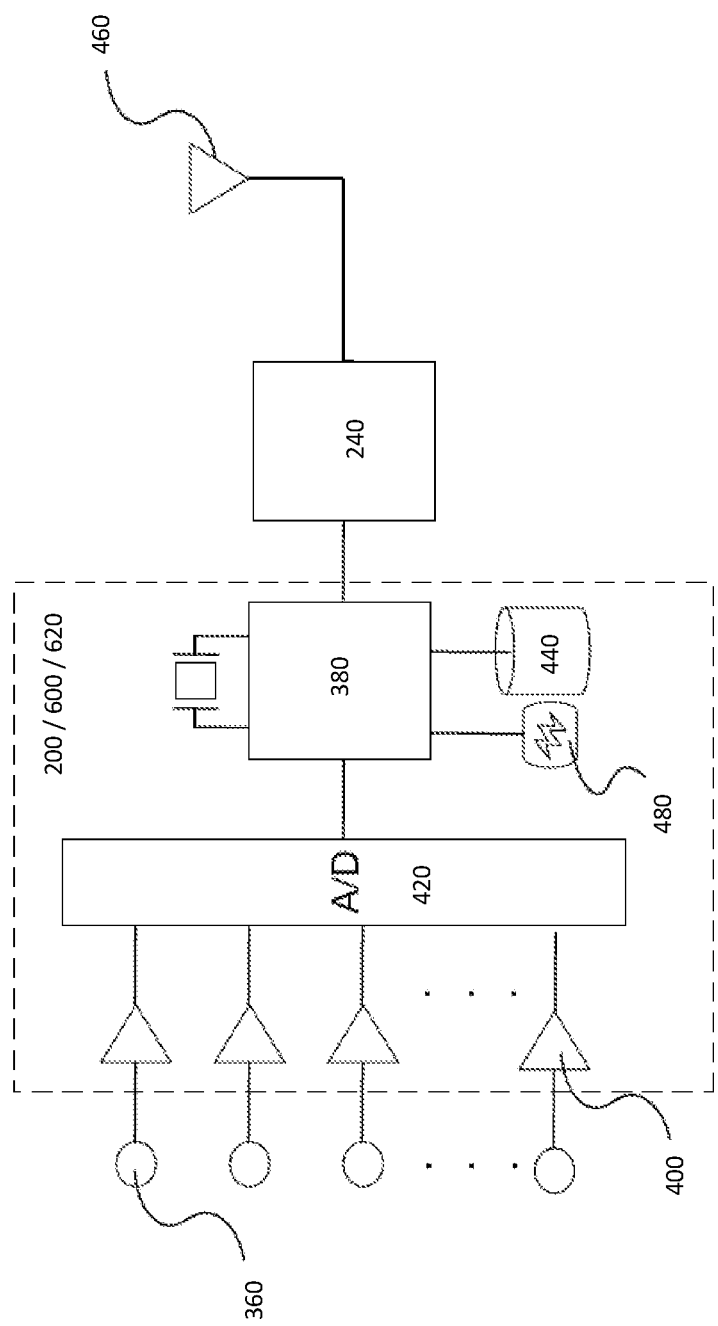

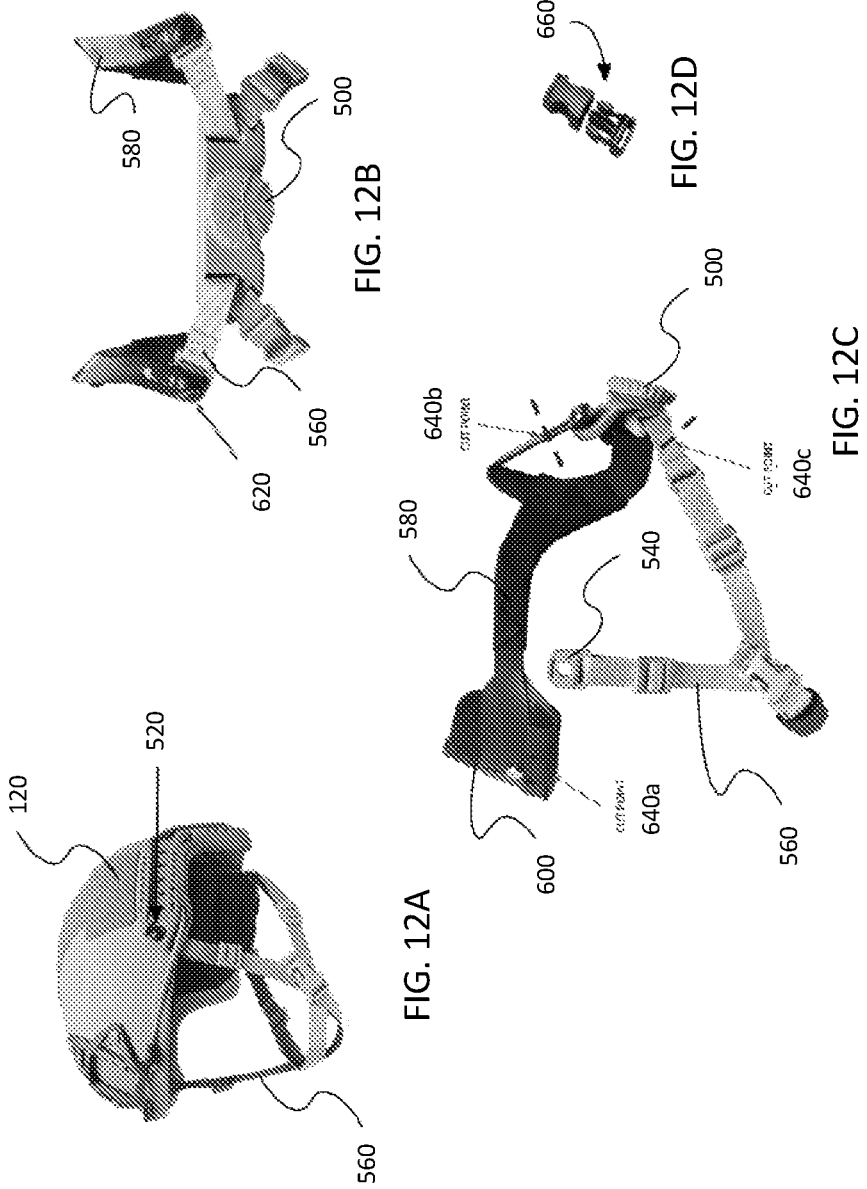

TRAUMA SCENE MONITORING SYSTEM

RELATED APPLICATIONS

This is a NONPROVISIONAL of, claims priority to, and incorporates by reference U.S. Provisional Application No. 62/845,444, filed May 9, 2019.

FIELD OF THE INVENTION

The present invention relates generally to a trauma scene monitoring system that integrates medic-worn appliances, patient-worn monitoring sensors, and a remote station where telemetry from each of these devices can be viewed, assessed, and acted upon in support of a field medic's first aid actions.

BACKGROUND

Battlefields and other scenes, e.g., traffic accidents, ski accidents, worksites, etc., are often associated with medics and other emergency personnel responding to life-threatening injuries. While the medics and others sometimes work as a team, it is not uncommon, especially at scenes involving multiple traumas, for these individuals to have to work alone under very stressful conditions. These individuals are often called upon to make life or death decisions in limited time with limited information. Moreover, they are often expected to report their actions to others both during and after completion of the medical intervention activities to which they attend.

SUMMARY OF THE INVENTION

A trauma scene monitoring system according to one embodiment of the present invention includes a medic-worn illumination device, a casualty-worn informatics system, and a remote monitoring station. The illumination device includes a frame with boom-mounted light sources positioned below the wearer's eyes near the zygomatic bones, thus orienting the light sources to project light in the direction of the wearer's view. Also included are audio/video means to capture audio/video information from a scene attended by the medic, and a telemetry unit to transmit that information to the remote monitoring station. The casualty-worn informatics system is integrated within a band worn by a monitored individual. The informatics system includes sensors to provide the monitored individual's vital statistics and a telemetry unit to transmit data concerning the monitored individual to the remote monitoring station. An optional indicator to display information regarding the monitored individual's vital statistics may also be included. At the remote monitoring station, receiving and presentation stations provide views of the data concerning the monitored individual and audio/video data from the medic-worn illumination device.

These and further embodiments of the present invention are discussed in more detail below.

BRIEF DESCRIPTION OF THE DRAWINGS

The present invention is illustrated by way of example, and not limitation, in the figures of the accompanying drawings, in which:

FIG. 4 is a rendering that shows front and back perspective views of a head-mounted illumination device configured in accordance with an embodiment of the present invention, as well as a side profile of such an illumination device as worn by a user.

FIG. 5 illustrates additional rear-side profiles views of an illumination device such as that shown in FIG. 4 as worn by a user.

FIG. 10 shows an alternative embodiment of the casualty-worn informatics system in which a sensor package is mounted to an elastic or other sizeable strap that is fittable about the wearer's head or other body part.

FIG. 11 illustrates an example of a sensor package of the casualty-worn informatics system.

FIGS. 12A-12D illustrate aspects of a helmet retention system that includes a casualty-worn informatics system configured in accordance with an embodiment of the invention.

FIG. 13 shows yet a further embodiment of a casualty-worn informatics system configured in accordance with an embodiment of the present invention.

DESCRIPTION

Figure 1B:
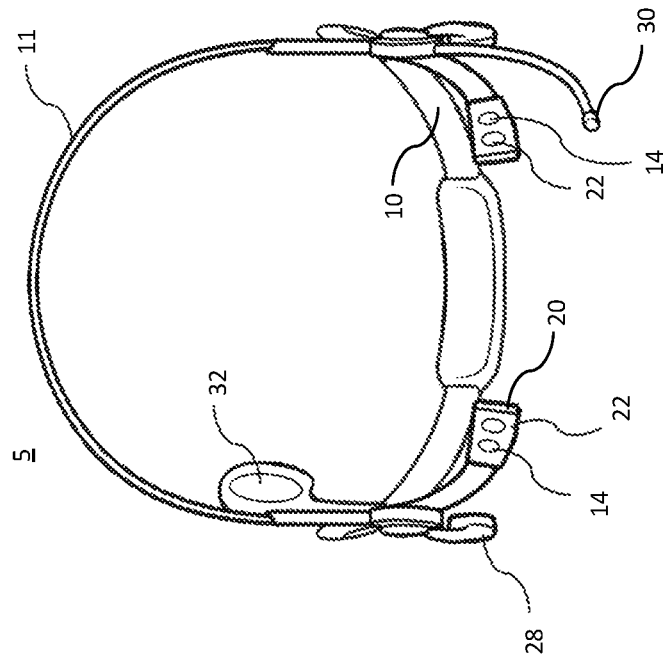
FIG. 1B is a front view of the head-mounted illumination device shown in FIG. 1A.
Figure 1A:
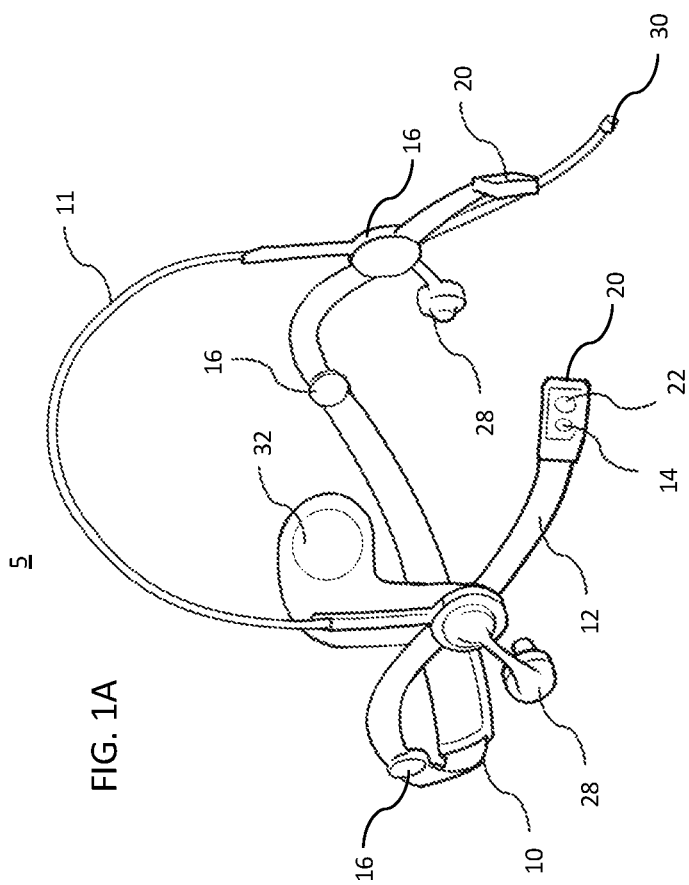
FIG. 1A is an isometric view of a head-mounted illumination device configured in accordance with an embodiment of the present invention.
Figure 1C:
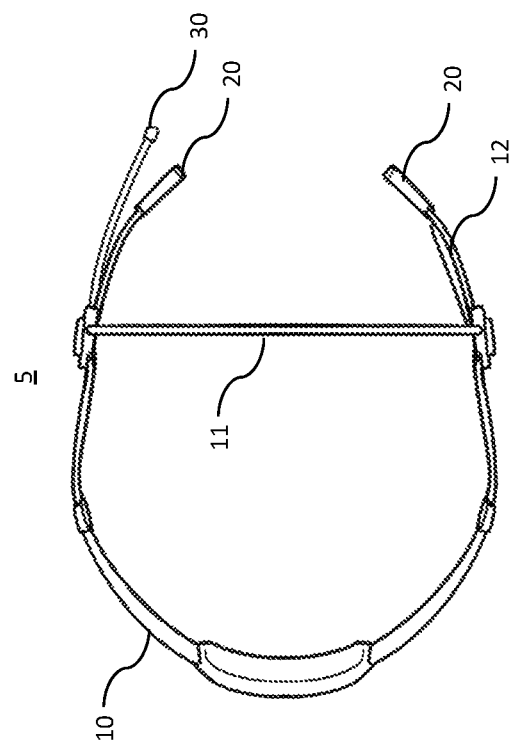
FIG. 1C is a partial side view of the head-mounted illumination device shown in FIG. 1A.
Figure 1D:
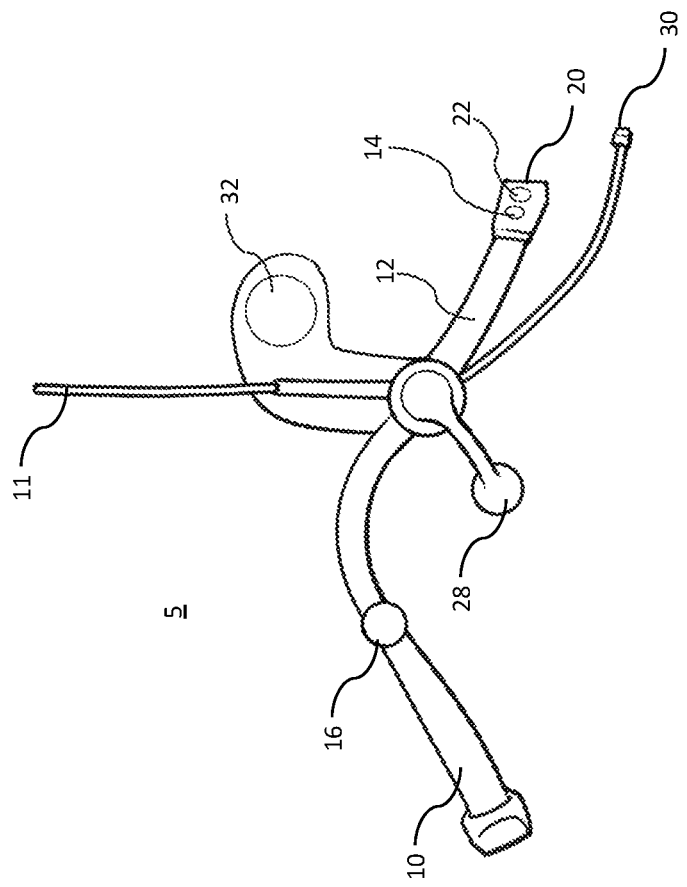
FIG. 1D is a top view of the head-mounted illumination device shown in FIG. 1A.

Described herein is a trauma scene monitoring system, which, according to one embodiment of the present invention, includes a medic-worn illumination device, a casualty-worn informatics system, and a remote monitoring station.

Illumination devices of the kind utilized as part of the present trauma scene monitoring system may be mounted on or in a frame intended to be worn on the person of a user (e.g., a medic or other first responder), for example, on the user's head. Unlike helmet-mounted lights, which require the user to wear a helmet in order to use them, illumination devices configured in accordance with embodiments of the present invention can be worn with or without a helmet or other eyewear, communication devices, visioning systems, etc. In particular, illumination devices configured in accordance with embodiments of the present invention provide directional lighting from the area of the user's zygomatic bones. Placing the light source in this vicinity reduces light-blinding of others when communicating. Additionally, the use of two (left-side and right-side), independently adjustable light sources allows for illumination of two areas simultaneously, at two separate color wavelengths if desired. Moreover, illumination devices configured in accordance with embodiments of the present invention provide a relatively small (in terms of area being occupied), augmentative, illumination source that does not interfere with eye protection, loupes, masks, etc. Such illumination devices allow users to avoid shadowing that occurs within cavities when using other light sources.

In addition to lighting, the frame carrying the illumination devices provides a platform for image and/or video capture and/or projection devices, for example as may be used with a helmet-worn or other heads-up display. Further, one or more microphones may be provided integral to or on the frame and/or on a boom associated with the frame that supports the illumination units. Hands-free operation of the present illumination devices may be facilitated using a boom microphone, an integral microphone, a chin-worn actuator that can be pressed against the wearer's shoulder, or a remote switch that can be activated (e.g., by voice command or otherwise) when worn under garments, for example as a pendant worn around the neck.

Embodiments of the informatics system can be head-worn, e.g., under a helmet, or worn about other body parts and used to provide a wearer's vital statistics and other information to the remote monitoring station, for example in connection with pre-hospital emergency care. In one embodiment, the informatics system is included within or mounted to a harness (e.g., a helmet retention system with a dial tensioning mechanism) that remains on a wearer's head after the helmet is removed. Thus, monitoring of the wearer's vital signs and other biometric information and telemetry are not interrupted by removal of the helmet.

1. The Illumination Device.

FIGS. 1A-1D and 2A-2C illustrate embodiments of a head-mounted illumination device 5 configured in accordance with the present invention. As shown, individual illumination elements, e.g., light emitting diodes (LEDs) 14, are included on or in a harness 10, which is worn over the ears and behind the head, and which may include an optional retracting head strap 11 connecting the two sides of the harness. At the front of the harness are located one or more booms 12 that extend over a portion of the wearer's face, below the eyes, and terminate in the area of the zygomatic bones. Two such booms, one each on the left side and right side of the wearer's face are shown in the illustrations, however, embodiments of the invention may provide just a single such boom on one side of the wearer's face, or multiple such booms on each side of the wearer's face. For some specialized applications it may be desirable to have different numbers of booms on each side of a wearer's face. The booms may or may not contact the wearer's face and may include a rubberized or other backing to provide a comfortable surface against the wearer's cheek.

Each of the booms 12 terminates with a hinged panel 20. The hinged panels are swivelly mounted to the booms, e.g., with a piano hinge, butt hinge, barrel hinge, butterfly hinge, pivot hinge, spring hinge, or other arrangement, and may be detachable from the boom so as to be replaceable/reconfigurable. For example, different arrangements of hinged panels 20 may be adapted to carry different illumination devices, sensors, imaging devices, and/or projection devices. In some examples, hinged panels 20 may be adapted for carrying LEDs that emit light in the visible spectrum. Other forms of hinged panels 20 may be adapted to carry LEDs that emit light in other wavelengths, in addition to or in lieu of the LEDs that emit light in the visible spectrum. Still further forms of hinged panels 20 may be adapted to carry light detectors and/or imaging devices (e.g., still image and/or video cameras), in addition to or in lieu of the LEDs that emit light in the visible spectrum. Also, as discussed below, some hinged panels 20 may be adapted to carry LEDs that emit light as well as image/video projectors for use with a heads-up display or other imaging system. Although the majority of the remaining discussion focuses on hinged panels adapted to carry LEDs that emit light in the visible spectrum, this discussion applies equally to the other forms of hinged panels and associated illumination, projection, and imaging devices described herein. Cabling for the illumination devices and other sensors, etc. may be provided by wiring run through hollow channels within the hinged panels, booms and harness (not shown). In instances where the hinged panels 20 are detachable from the booms 12, electrical contacts may be placed on both sides of the hinged panel-boom junction so as to provide electrical continuity and avoid the need for separately coupled wirings (although such wired connections may be used).

In some instances, the illumination may be provided by fiber optic cables terminating (e.g., with or without lens systems) at the hinged panels, in which case the illumination source may be positioned remotely from the hinged panel, for example worn elsewhere on the person of the user such as in a shoulder harness or utility belt. This would allow for larger power sources and illumination sources of significant luminance, while still providing the directional control afforded by the use of the harness and boom system of the present invention. Likewise, image capture components, such as imaging systems and storage devices could be worn on a shoulder harness or belt and the information obtained by image sensors positioned in the hinged panels 20 at the ends of booms 12 conveyed to such systems through the use of fiber optic waveguides routed through channels in the present headwear.

The illustrated example of the hinged panels 20 at the ends of booms 12 are sized so as to provide one or more LEDs (and/or other sensors and/or projecting elements) approximately below the wearer's eye(s) and facing forward, in the direction the wearer is looking, so that the LEDs illuminate the area of interest to the wearer. The booms 12 are sized so as to position the hinged panels 20 so that they just rest on the wearer's cheeks, preferably over the zygomatic bones, without putting undue pressure thereon. Accordingly, harnesses 10 may be provided in various sizes to accommodate head sizes and shapes of different wearers, or they may be adjustable at one or more points to accomplish same. In some instances, harnesses and booms may be personalized to a wearer by creating a model, either physical or digital, of the wearer's head and face and fabricating a harness specifically to suit the wearer according to the dimensions provided from the model. Modern additive manufacturing processes (commonly known as 3D printing) make such customizations economically feasible even for consumer applications and custom harnesses could readily be produced from images of a wearer's head and face captured using computer-based cameras and transmitted to remote server hosting a Web service for purchase of the harness and accessories therefor. For example, following instructions provided by the Web-based service, a user may capture multiple still images and/or a short video of his/her head and face. By including an object of known dimensions (e.g., a ruler, a credit card, etc.) within the field of view of the camera at the approximate position of the user's head as the images are captured, a 3D model of the user's head and face can be created at the server. The user can then be provided with an opportunity to customize a harness to be sized to the dimensions of the model, selecting, for example, the number of booms, the type and number of hinged panels, with illumination or other accessories, the positions over the ears, etc. at which the harness will be worn, and other parameters of the to-be-manufactured harness. Once the customizations are specified, and payment collected, the harness specification may be dispatched to a manufacturing facility at which the harness is fabricated.

Figure 2A:
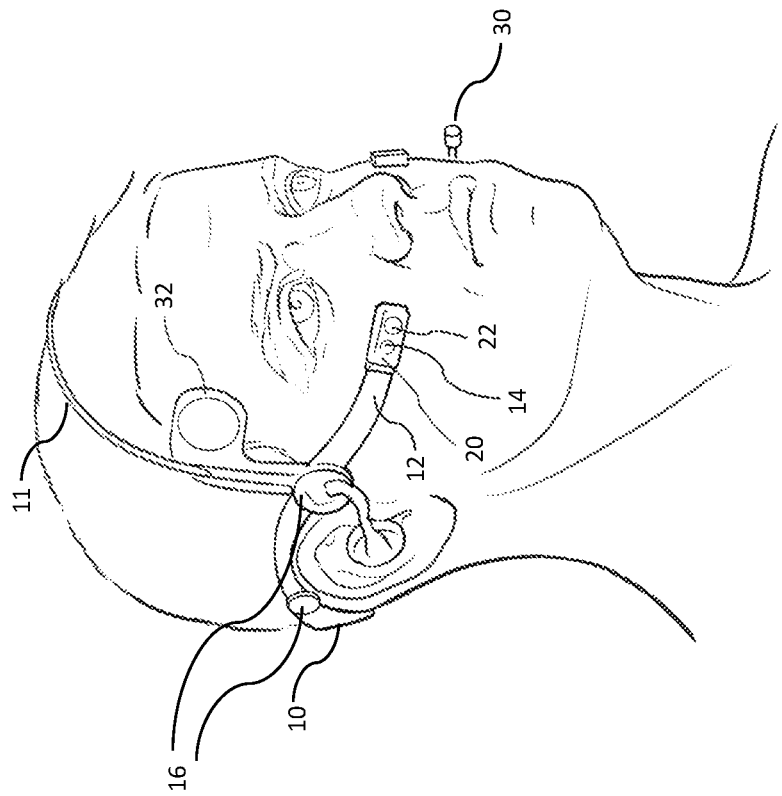
FIGS. 2A-2C illustrate aspects of a head-mounted illumination device configured in accordance with an embodiment of the present invention as worn by a user.
Figure 2B:
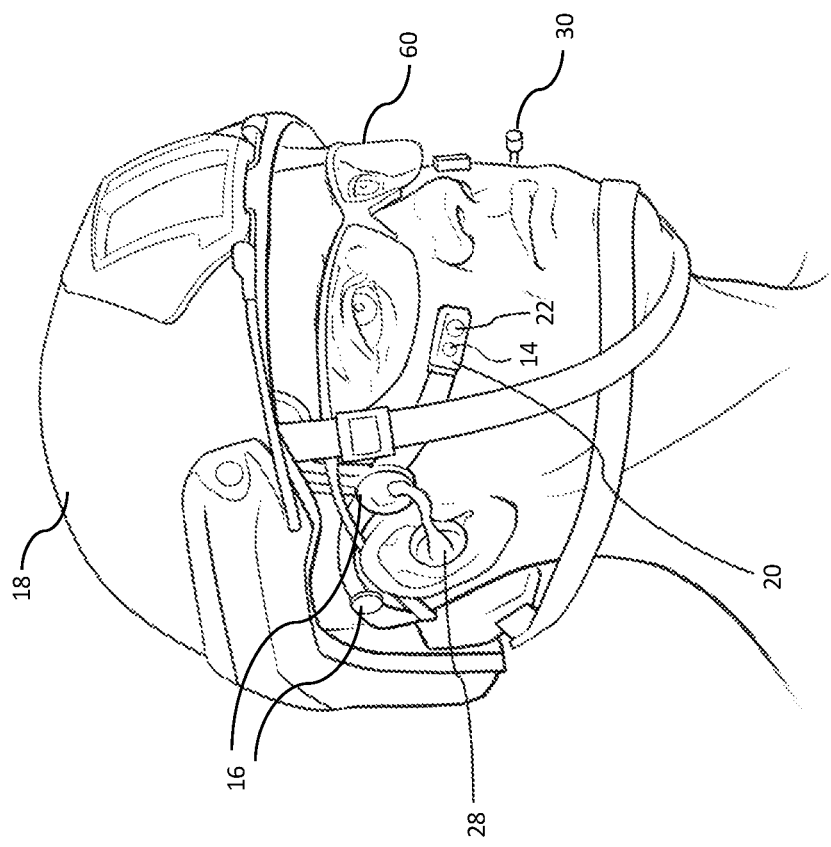

The harness 10 may include one or more hinge points 16, one or more on each side, about which sections of the harness may articulate so as to allow for a comfortable fit on the wearer. This may be especially important in harnesses that are not fabricated for personalized fit, so as to allow individual wearers to achieve a comfortable fit. As shown in FIG. 2A, the harness 10 may be worn next to the head, beneath a helmet 18. Accordingly, by allowing the harness 16 to articulate in several places, the fit of the harness may be adjusted to accommodate the presence of the helmet and its associated retention straps, as well as other helmet-worn accessories such as a screen 24 of a head-up display (see FIG. 2C).

The hinge points 16 may be purely friction fit adjustments in which the relative friction between opposing cylindrical ribs is sufficient to keep the relative orientation of two hinged members constant during wear. Or, the hinge points may incorporate ratchet fittings that provide interlocking gear-like rings to assure that the relative positions of two members will not change with respect to one another unless a relatively significant force is applied. Other hinged arrangements may be used at points 16, such as swivel torque hinges, circle rotational hinges, click and pawl mechanisms, etc. In some cases, the hinge points 16 are fitted with O-rings to prevent moisture from intruding.

Figure 3B:
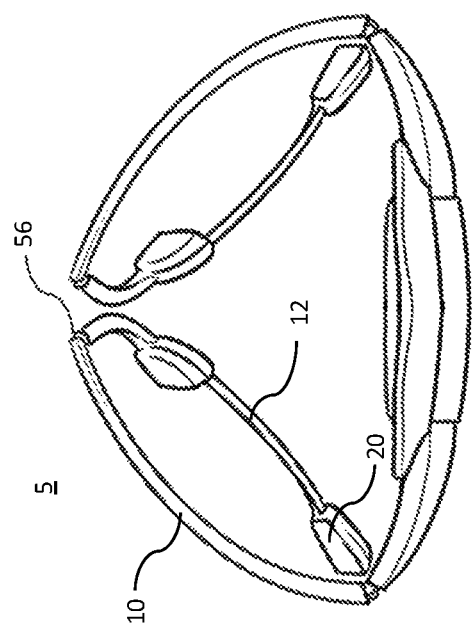
FIGS. 3A and 3B illustrate aspects of the hinged articulation of a head-mounted illumination device configured in accordance with an embodiment of the present invention that allow the head-mounted illumination device to be folded when not in use.
Figure 3A:
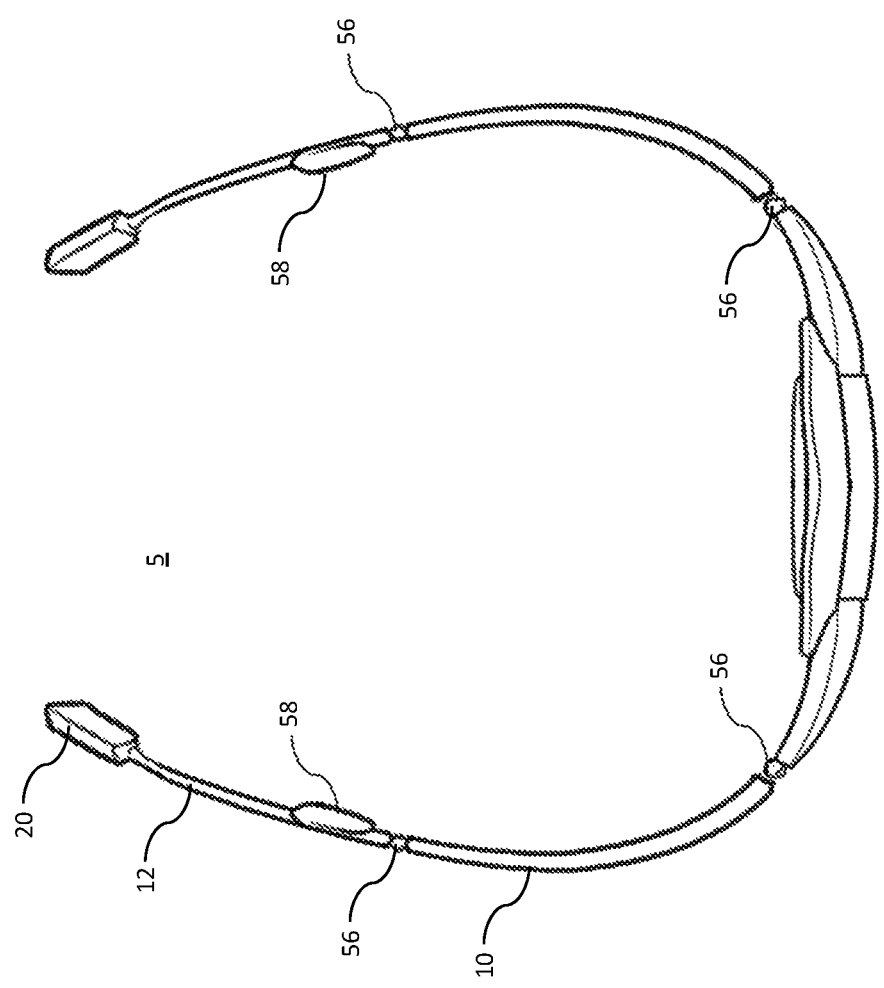

Referring briefly to FIGS. 3A and 3B, in some embodiments additional hinge points 56 may be provided along booms 12 to allow the harness 10 to be folded into the configuration shown in FIG. 3B, with the booms folded inwards towards the rear of the harness. This allows easy storage of the harness while preventing accidental damage to the booms. As shown in FIG. 3A, one or more hinge points 56 may be included along the length of each boom, providing multiple points of articulation. The hinges used at hinge points 56 may be any of piano hinges, butt hinges, barrel hinges, spring hinges, or other arrangements.

Additionally, one or more grip points 58 along the inner surface of each boom 12 or other parts of harness 10 may be fitted with silicone pads for contacting the wearer's skin. The pads assist in reducing slipping of the harness when worn, and also distribute pressure over a larger surface area than might otherwise be the case if they were not present. While silicone pads are preferred, pads made of other materials, e.g., cork, may be used.

Figure 2C:
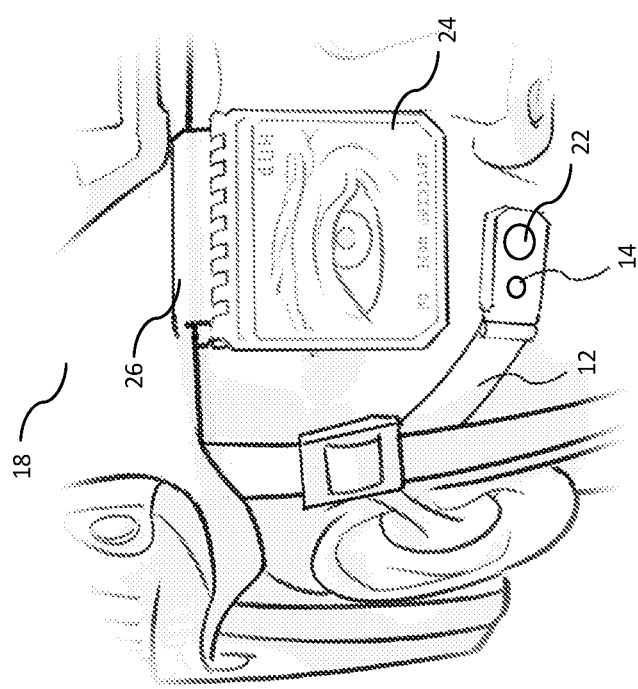

Referring back to FIGS. 1A-1D and 2A-2C, one or more LEDs 14 may be included in each hinged panel 20 at the end of each boom 12. In addition to the LED(s), the hinged panels 20 may include heads up display (HUD) projection optics 22. As shown in FIG. 2C, the HUD projection optics 22, which are oriented towards the wearer's eye, may be used to project information on a HUD screen 24 disposed in front of the wearer's eye(s). The screen 24 may be secured to helmet 18 on a hinge 26 so that it can be swiveled out of the wearer's line of sight when not in use, or it may exist in the form of a screen 60 worn in front of the wearer's eyes in a fashion similar to a pair of spectacles (see FIG. 2A). Alternatively, the projector may be oriented away from the user so that images can be projected onto a surface in front of the user. A power source and telemetry transmitter (e.g., for HUD data and audio communications) may be included in the harness 10 and/or a helmet 18 and attached to the various illumination and video elements, microphone(s), and earpiece(s) via one or more wire leads within the harness.

FIG. 4 is a rendering that shows front and back perspective views of a head-mounted illumination device configured in accordance with an embodiment of the present invention, as well as a side profile of such an illumination device as worn by a user. FIG. 5 illustrates additional rear-side profiles views of such an illumination device as worn by a user.

Returning to FIGS. 1A-1D, the harness 10 may further support one or more communication earpieces 28. Together with one or more boom microphones 30, which may be supported on one or more booms separate from that used to carry hinged panels 20 (or, in some embodiments, on the same boom), the earpiece and microphone allow for communications to/from the wearer. The earpiece and microphone may be communicatively connected to a transceiver carried elsewhere on the wearer's person, either using wired or wireless connections.

In other embodiments, the earpiece 28 and/or microphone 30 may be eliminated, and audio communications facilitated through bone conduction elements. Portions of the harness 10 are in contact with the wearer's head. Hence, rather than an earpiece, a bone conduction headphone that decodes signals from a receiver and converts them to vibrations can transmit those vibrations directly to the wearer's cochlea. The receiver and bone conduction headphone(s) may be embedded directly in the harness 10, or in some cases the receiver may be external to the harness. One or more bone conduction headphones may be provided. For example, the headphone(s) may be similar to bone conduction speakers employed by scuba divers and may consist of a piezoelectric flexing disc encased in a molded portion of the harness 10 that contacts the wearer's head just behind one or both ears. Similarly, a bone conduction microphone may be provided in lieu of a boom microphone.

In some embodiments, harness 10 may include a sensor package 32 that allows for monitoring of the wearer's vital statistics. A power source and telemetry transmitter (not shown) may be included in harness 10 and attached to the sensor package via one or more wire leads. Thus, even with a helmet removed, the sensors package 32 can continue to relay information concerning the wearer's vital statistics and other monitored biometrics via the telemetry transmitter, because harness 10 remains attached to the wearer.

The sensor package may include a sensor pads constructed of conductive fabric that contact the wearer at or near the temple. Additional sensor pads may be integrated in the harness 10 or may be included in the retractable strap positioned over the head of the wearer. This would allow for additional sensor readings for electrophysiological or other noninvasive monitoring of the wearer.

Figure 6:
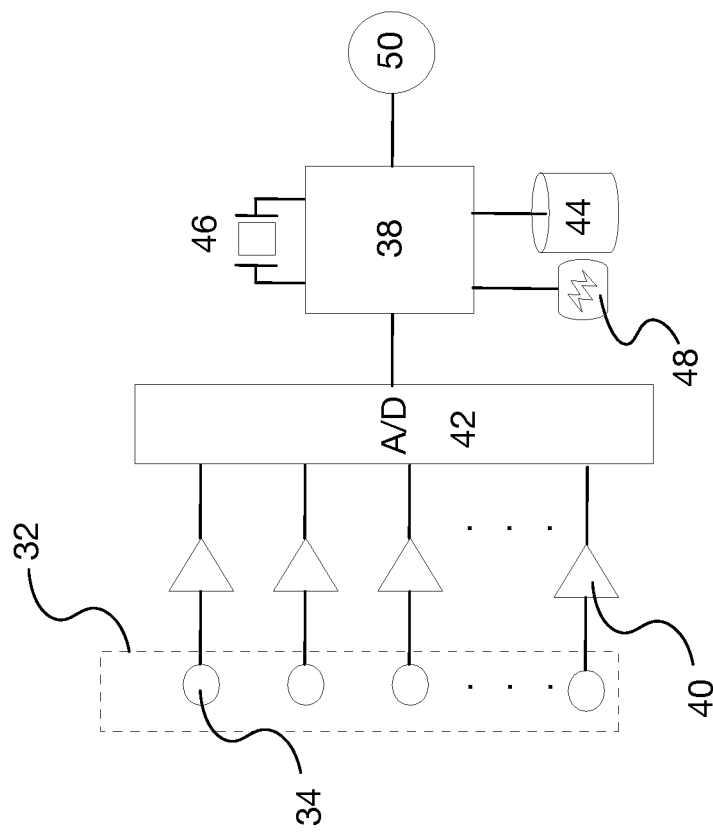
FIG. 6 illustrates an example of a sensor package arrangement for optional use with the head-mounted illumination device of the present invention.

The sensor pad(s) and associated electronics may allow for detection of electrical signals in the manner described by von Rosenberg, W. et al., "Smart Helmet: Monitoring Brain, Cardiac and Respiratory Activity," Conf. Proc. IEEE Eng. Med. Biol. Soc. 2015, pp. 1829-32 (2015). For example, as shown in FIG. 6, sensor pad(s) 34 may be attached by electrical leads to a processor 38, e.g., via associated amplifiers 40, analog-to-digital converters 42, etc., which samples the signals from the sensor pads periodically. A record of the sampled signals may be stored locally, e.g., in a suitable writable memory 44 such as a flash memory, and also may be transmitted to a remote monitoring location via a telemetry transmitter 48 and an associated antenna. Alternatively, the telemetry may be transmitted only when the transmitter is activated, e.g., by an on-scene paramedic, or by the wearer him/herself. Upon command, any stored samples may be similarly transmitted so that a history of the wearer's biometric and vital signs can be analyzed by a physician or other person at the remote monitoring station, or locally via an output port 50.

In some embodiments, the sensor package may also include one or more accelerometers 46 which provide inputs to processor 38 concerning rapid accelerations/decelerations of the wearer's head. Such measurements may be important when assessing possible traumatic brain injuries, cervical spinal injuries, and the like.

Although not shown in the various views, a power source for the electronics is provided and may be housed within the harness 10 or located external thereto (e.g., worn on a vest or pack). In some cases, a primary power source may be located external to the harness 10 and a secondary power source provided integral thereto. This would allow the primary power source to be decoupled from the harness, which would then revert to using the secondary power source (e.g., a small battery or the like), at least temporarily. This would allow for continuous monitoring of the biometric and vital signs and provision of related telemetry. Primary power may later be restored by an attending medic using a transportable power supply. To facilitate this operation, the harness may be provided with one or more ports allowing connection of different forms of power supplies.

Beyond comfort, the present head-worn illumination device offers beam separation/brightness consistency when closing distance/peering. For example, by having separate illumination sources on booms on either side of a wearer's face, with each being mounted on a pivotable, hinged panel, a wearer can aim each illuminations source independently so as to provide for combining the illumination of the respective beams at a desired point in front of the wearer (e.g., corresponding to an area of interest to the wearer), so as to maximize the provided illumination at that point. Then, by moving his/her head towards/away from the area of interest, the user can provide a form of brightness control over that area of illumination. As the user moves his/her head, the beams provided by the illumination sources will separate, thereby adjusting the effective amount of illumination at the area of interest. In some embodiments, haptic feedback may be used for various indications, e.g., low battery, etc. Embodiments of the head-worn illumination device may also support other components of a head-worn "system" that includes integrated eyewear components, disposable masks and caps, heads-up display, sensors, data capture components, etc.

Illumination devices of the kind described herein, and especially the harness, booms, and hinged panels thereof, may be fashioned from a variety of materials, including but not limited to plastics (e.g., zylonite), metals and/or metal alloys, carbon fiber, wood, cellulose acetates (including but not limited to nylon), natural horn and/or bone, leather, epoxy resins, and combinations of the foregoing. Fabrication processes include, but are not limited to, injection molding, sintering, milling, and die cutting. Alternatively, or in addition, one or more additive manufacturing processes, such as extrusion, vat photopolymerization, powder bed fusion, material jetting, or direct energy jetting, may be used to fashion the illumination device and/or components thereof.

2. The Informatics Sensor.

Figure 7:
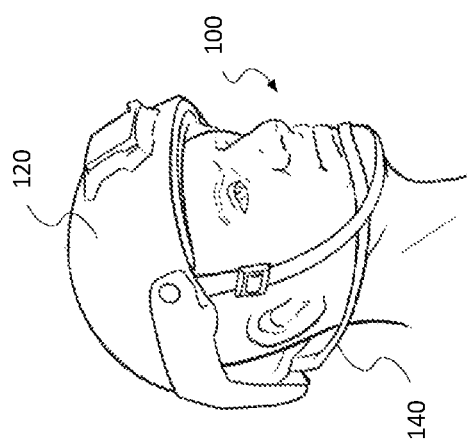
FIG. 7 illustrates an individual wearing a helmet that includes a retention system incorporating a casualty-worn informatics system configured in accordance with an embodiment of the invention.

FIG. 7 illustrates an individual 100 wearing a helmet 120. The helmet is secured to the individual's head by means of a retention system 140. In this example, the retention system includes a plurality of straps that pass across the wearer's chin, either directly or with a chin guard, allowing the helmet to be positioned squarely on the wearer's head with the front of the helmet protecting the wearer's forehead and the back of the helmet positioned approximately adjacent the nape of the wearer's neck. The straps of the retention system are adjusted, typically using a ratchet system and/or one or more buckles, so that the helmet sits squarely and securely on the wearer's head with the straps just below and in front of the ears.

Figure 9:
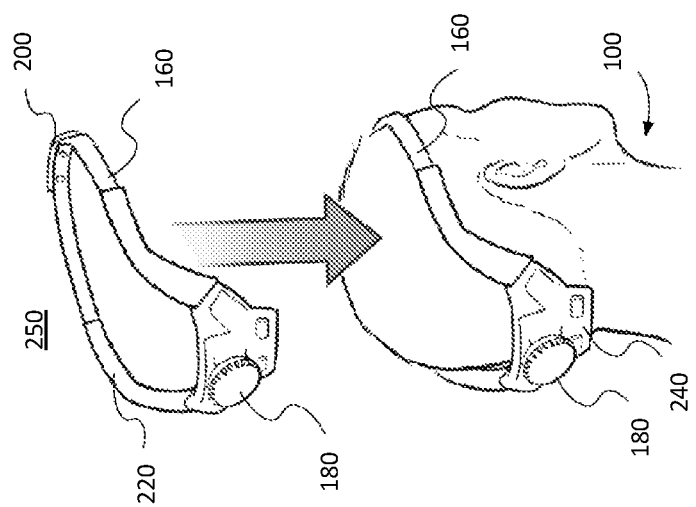
FIG. 9 illustrates how the headband section of the retention system fits over the wearer's head.
Figure 8:
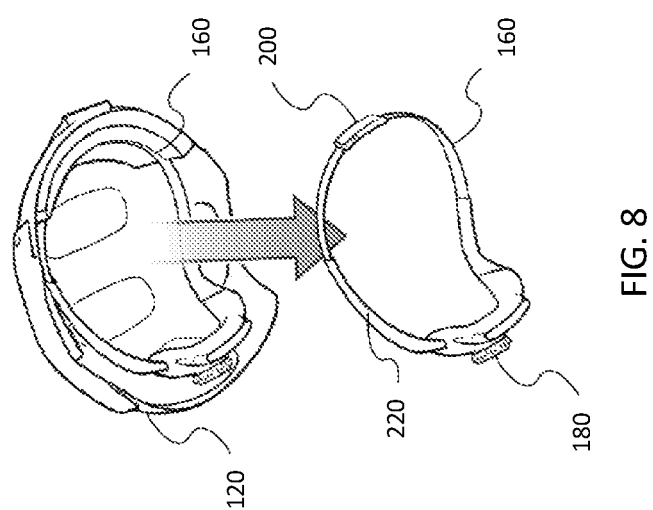
FIG. 8 shows an underside view of the helmet shown in FIG. 7, exposing a portion of the retention system in the form of a headband.

FIG. 8 shows an underside view of helmet 120 (top view) exposing a portion of the retention system 140 in the form of a headband 160. For clarity, the straps are not shown in this view. The straps may be removable from the retention system 14. FIG. 9 illustrates how the headband section 160 of the retention system 140 fits over the wearer's head.

As illustrated in these views, headband 160 is fitted over the wearer's head and sized using the dial/ratchet adjustment mechanism 180 located at the back of the headband. When headband 160 is secured within helmet 120, for example using snaps, hook and loop, or other fastening means, adjusting the fit of headband 160 using the ratchet will thus secure the helmet to the wearer's head. However, because the headband 160 is only removably secured within the helmet 120, the helmet 120 can be taken off of the wearer's head while leaving the headband 160 in place (as shown in FIG. 9). Headband 160 includes a sensor package 200 that allows for monitoring of the wearer's vital statistics. A power source and telemetry transmitter 240 may be included in headband 160 and attached to the sensor package via one or more wire leads 220. Thus, even with the helmet removed, the sensors package 200 can continue to relay information concerning the wearer's vital statistics and other monitored biometrics via the telemetry transmitter, because headband 160 remains attached to the wearer. Collectively, the headband, sensor package, and telemetry transmitter (which may, in some instances, be located separately from the headband) form an informatics sensor 250.

FIG. 10 shows an alternative embodiment in which the sensor package 200 is mounted to an elastic or other sizeable strap 260 that is fittable about the wearer's head or other body part. In this embodiment, the strap 260 is not part of the helmet retention system per se, but instead is separately secured to an existing helmet retention system 280 associated with helmet 120. The helmet retention system 280 may include a ratchet/dial-like adjustment means 300 and the strap 260 may be secured to a harness portion of the helmet retention system using hook and loop fasteners 320, snaps, or other fastening means. Strap 260 includes integral wire leads (not shown in these views) that electrically connect sensor package 200 to a power source and telemetry transmitter 340 in the helmet retention system. In this embodiment, the strap 260 and sensor package may be temporarily removed from a wearer's head when the helmet is removed, quickly detached from the helmet retention system, and then replaced on the wearer's head. Although this will entail a brief period of time when the wearer's vital statistics, etc. are not being monitored through the sensor package, it nevertheless provides an effective means for near-continuous provision of same and effective pre-hospital emergency care monitoring.

Yet a further embodiment is illustrated in FIGS. 12A-12C. In this example, a helmet 120 has an associated retention system that includes a plurality of straps (e.g., chin straps) 560, a headband arrangement 580 that is secured to an interior of the helmet, and an associated ratchet tensioning means 500. The straps are secured near the temple portion of helmet 120 by bolts 520 which pass through eyelets 540. By adjusting the ratchet 500, the headband arrangement 580 and/or the straps 560 are tightened or loosened, thereby fitting the helmet to the wearer's head. In accordance with the present invention, sensor arrangements 600, 620 are included in portions of the headband arrangement, for example near the forehead and behind the ears of the wearer. As with the above-described embodiments, a power source and telemetry transmitter may be included in headband arrangement and/or the ratchet tensioning means and attached to the sensor package(s) via one or more wire leads.

In this example, the helmet may be removed while leaving the headband arrangement and sensor package(s) in place by physically cutting the helmet off of the wearer at one or more points 640a-640c. For example, the headband arrangement may be severed at a cut point 640a near the forehead and at a cut point 640b behind the ears of the wearer. Straps 560 may be severed at a cut point 640c behind the head of the wearer, allowing the helmet to be fully removed. In this way, removal of the helmet will not cause removal of the sensor arrangement(s). Alternatively, one or more of the headband arrangement and/or straps may be filled with quick release buckles 66 (see FIG. 12D), pins, or other arrangement, to allow for removal of the helmet without the need to cut the straps, etc.

As illustrated in FIG. 11, the sensor package(s) 200, 600, 620, included in the above-described embodiments may be electrically coupled to one or more sensor pads 360 constructed of conductive fabric that contact the wearer at the forehead and elsewhere (e.g., the nape of the neck, the temples, etc.). One or more of the sensor pads may be integrated in the headband 160, 580. Alternatively, or in addition, sensor pads may be included in a plurality of straps to be positioned over the head of the wearer or in a cap-like garment worn under the helmet. This would allow for additional sensor readings for electrophysiological or other noninvasive monitoring of the wearer.

The sensor pads 360 and associated electronics may allow for detection of electrical signals in the manner described by von Rosenberg et al. For example, the sensor pads may be attached by electrical leads to a processor 380, e.g., via associated amplifiers 400, analog-to-digital converters 420, etc., which samples the signals from the sensor pads periodically. A record of the sampled signals may be stored locally at the helmet, e.g., in a suitable writable memory 440 such as a flash memory, and also may be transmitted to a remote monitoring location via the telemetry transmitter 240 and an associated antenna 460. Alternatively, the telemetry may be transmitted only when the transmitter is activated, e.g., by an on-scene paramedic, or by the wearer him/herself. Upon command, any stored samples may be similarly transmitted so that a history of the wearer's biometric and vital signs can be analyzed by a physician or other person at the remote monitoring station.

In some embodiments, the sensor package 200 may also include one or more accelerometers 480 which provide inputs to processor 380 concerning rapid accelerations/decelerations of the wearer's head. Such measurements may be important when assessing possible traumatic brain injuries, cervical spinal injuries, and the like.

Although not shown in this view, a power source for the electronics is provided and may be housed within the retention system or located external thereto (e.g., worn on a vest or pack). In some cases, a primary power source may be located external to the other components of the system and a secondary power source provided integral thereto. This would allow the primary power source to be decoupled from the system, which would then revert to using the secondary power source (e.g., a small battery or the like), at least temporarily. This would allow for continuous monitoring of the biometric and vital signs and provision of related telemetry. Primary power may later be restored by an attending medic using a transportable power supply. To facilitate this operation, the system may be provided with one or more ports allowing connection of different forms of power supplies. Importantly, in embodiments of the invention, removal of the helmet does not dissociate the sensor pads and associated electronics from the wearer. Thus, recording and telemetry of the wearer's vital statistics and other biometric information, e.g., via the sensor pads, does not stop when the helmet is removed.

FIG. 13 shows yet a further embodiment of a casualty-worn informatics system integrated within a band 260 configured to be worn by a monitored individual. As before, the band or strap 260 is fittable about the wearer's head or other body part and may, but need not necessarily be, part of a helmet retention system or separately securable to an existing helmet retention system associated with helmet. As before, strap 260 includes integral wire leads (not shown in this view) that electrically connects a sensor package 200 to a power source and telemetry transmitter. In this embodiment, the strap 260 is also fitted with an indicator 330, which in various embodiments may include a plurality of LEDs, one or more illuminated indicators, or other indicators, that provide an on-scene medic or a remote viewer observing a video feed from the medic-worn illumination device with an indication of the patient's vital signs. For example, the indicator 330 may be driven by an output of the processor 380 to illuminate LEDs as green, yellow, and/or red, so as to reflect the status of a patient's vital signs. Different ones of the LEDs (or other illumination devices) may be used to indicate different monitored body functions (pulse rate, temperature, etc.) as indicated by the sensor package 200. For example, green may indicate that the monitored body function is within normal/acceptable values, yellow that the monitored body function is outside the normal/acceptable values, and red that the monitored body function reflects a condition that requires immediate attention. Alternatively, or in addition, the indicator 330 may reflect changes in the patient's vital signs over time. For example, the indicator may provide a timeline view of changes in the patient's monitored body functions, with a trend from green to red or red to green, etc. The indicator thus provides an on-scene medic and/or others with a visual display reflecting a monitored individual's condition that can be understood at a glance. Such an indicator is therefore highly useful in situations involving mass casualties, where a single medic or a few individuals must attend to a number of patients.

3. Remote Monitoring Station(s).

Figure 14:
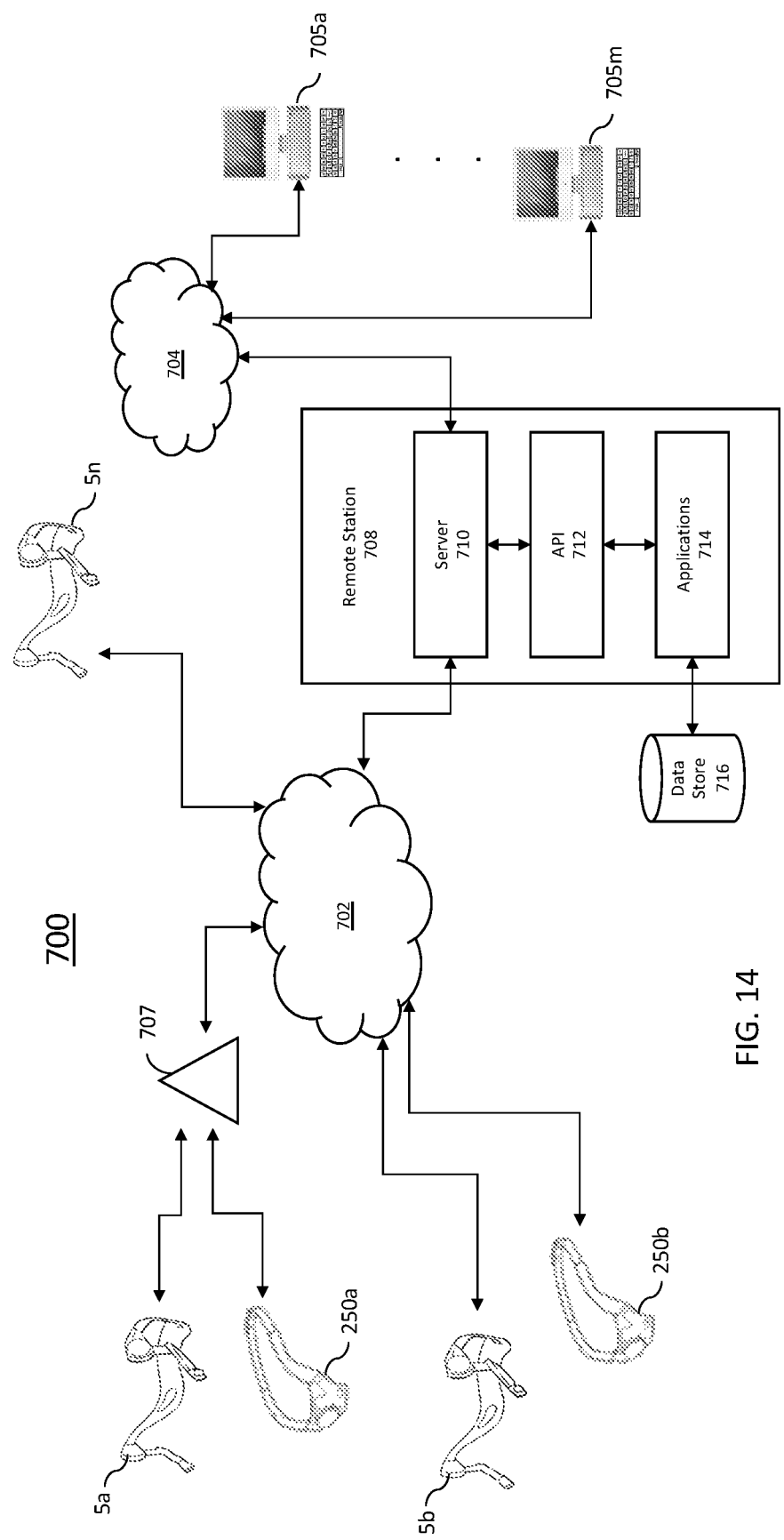
FIG. 14 illustrates an example of a trauma scene monitoring system that integrates medic-worn appliances, patient-worn monitoring sensors, and a remote station where telemetry from the medic-worn appliances and patient-worn monitoring sensors is collected, stored, analyzed, and made available for view in accordance with an embodiment of the invention.

Referring now to FIG. 14, an example of a trauma scene monitoring system 700 that integrates medic-worn appliances 5a, 5b, 5n, patient/casualty-worn monitoring sensors 250a, 250b, and a remote station 708 where telemetry from each of these devices is collected via one or more networks or network of networks 702 is shown. Included as part of the remote station 708 are one or more client stations 705a, 705m, each communicatively coupled to the remote station 708 by one or more networks or network of networks 704 and at which the collected telemetry can be stored, viewed, assessed, and acted upon in support of field medics' first aid actions. Some or all of the components of network 704 may be part of network 702 or they may be separate networks or networks of networks. A repeater unit 707, which may be stationary or mobile, is shown as providing a communication path for medic-worn appliance 5a and patient-worn monitoring sensor 250a to network 702. In practice, multiple repeater units may be used for such purposes to accommodate multiple medic-worn appliances and/or patient-worn monitoring sensors. Although only discrete numbers of medic-worn appliances, patient-worn monitoring sensors, client stations, and other components of system 700 are illustrated, in practice instantiations of the trauma scene monitoring system may have any number of such devices included. Likewise, although the remote station 708 is shown as a single unit, in practice the functions of the remote station may be distributed over a number of computer systems, for example, cloud-based computer systems that include multiple virtual machines running on a number of physical compute devices. The illustration of trauma scene monitoring system 700 should, therefore, be regarded as illustrative for purposes of the present description and not limiting in terms of the physical composition thereof.

In this illustrated embodiment, the trauma scene monitoring system 700 includes multiple medic-worn illumination devices, casualty-worn informatics systems, and a remote monitoring station, as well as means for intercommunication amongst these units. The illumination devices may be of the kind described above with a frame and boom-mounted light sources positioned below a wearer's eyes near the zygomatic bones, thus orienting the light sources to project light in the direction of the wearer's view. Also included are audio/video means to capture audio/video information from a scene attended by the medic-wearer, and a telemetry unit to transmit that information to the remote station 708. The casualty-worn informatics systems may be integrated within headbands worn by monitored individuals, as discussed above. The informatics systems include sensors to provide the respective monitored individual's vital statistics and a telemetry unit to transmit data concerning the monitored individual to the remote station 708. At the remote station 708, one or more client stations 705a-705m act as receiving and presentation stations to provide views of the data concerning the monitored individuals and audio/video data from the medic-worn illumination devices.

In general, the communications between medic-worn illumination devices 5a, 5b, 5n, and remote station 708 may be wireless radio frequency (RF) communications, at least in part. For example, the respective telemetry units of the medic-worn illumination devices may include RF transceivers to transmit and receive audio/video information to/from the remote station 708. Similarly, the telemetry units associated with the casualty-worn informatics systems may include RF transceivers to transmit information concerning the monitored individual's vial statistics to the remote station 708. In some cases, the casualty-worn informatics systems may be configured to make use of the telemetry units of the medic-worn illumination devices, for example using a local, short-range wireless communications connection thereto and/or a local wired communications connection thereto. In this latter case, in addition to information received from the sensors associated with the casualty-worn informatics systems, the medic-worn illumination devices may also communicate information from their own associated sensors (cameras, microphones, etc.) over network 702 to provide operators at the remote station 708 with a more complete description of the environment in which the medic associated with the casualty is operating.

In system 700, the medic-worn illumination devices 5a, 5b, 5n, may be configured to form a wireless ad hoc network, such as a mesh network, amongst some or all of them to wirelessly transmit data concerning the respective local environments to remote station 708 via network 702. Each medic-worn illumination device may be associated with a unique identifier that can be associated with audio/video information captured by the respective device in order to correlate that information with a location (e.g., derived from GPS receivers or other location units worn by the medics) and wearer. When the medic-worn illumination devices are configured as a mesh network, data transmissions from the trauma scene may be more robust than if communications were dependent upon transmissions from individual units, as multiple wireless connections to network 702 between the medic-worn illumination devices provide redundancy in such a topology. The casualty-worn informatics systems may also participate in such a network. For example, one or more medic-worn illumination devices (e.g., 5a) and/or casualty-worn informatics systems (e.g., 250b) may act as a relay, providing an indirect communication link between other medic-worn illumination devices and/or casualty-worn informatics systems and the network 702. So too may repeater 707 act as a relay station for one or more medic-worn illumination devices and/or casualty-worn informatics systems.

Within remote station 708, one or more computing devices communicatively coupled to network 702 hosts a server 710, such as an HTTP server, and an application 714 that implements aspects of the trauma scene monitoring system 700 in accordance with embodiments of the present invention. Application(s) 714 may perform coordination and analytics on data received from the medic-worn illumination devices, casualty-worn informatics systems, and other sensors (e.g., GPS units that provide location information, remote-piloted drones that provide scene-wide audio/video views, etc.) and store same in a data store 716. Data store 716 may be a dedicated storage appliance or may be cloud-based storage accessible to the computing devices that make up the remote station.

Application 714 may support an Application Programming Interface (API) 712 providing external access to client stations 705a-705m for accessing live audio/video feeds from the medic-worn illumination devices and casualty-worn informatics systems and/or from remote data store 716 via server 701. In certain embodiments, client applications such as web browsers running on client stations 705a-705m may access application 714 via its API 712 and through server 710 using protocols such as HTTP (hypertext transfer protocol) or FTP (file transfer protocol). In certain embodiments, various client stations 705a-705m may be a laptop or desktop computers, mobile devices such as smart phones, or wearable devices such as a virtual reality player.

The present system is suitable for both training and in-service operations. In one embodiment of the invention, when a medic or other first responder equipped with a medic-worn illumination device appears on the scene of a trauma event, he or she activates the telemetry unit of the medic-worn illumination device. In response, the telemetry unit begins transmitting audio/video information captured by the microphone(s) and camera(s) of the medic-worn illumination device to the remote station 708. In addition, if the person being attended to by the medic is wearing a casualty-worn informatics system, that unit will also provide telemetry to the remote station 708 concerning the wearer's vital statistics, etc. In some cases, the telemetry unit of the casualty-worn informatics system may not begin transmitting until activated by the on-scene medic, while in other cases such transmissions may occur even before a medic arrives on the scene.

At the remote station 708, the audio/video information from the medic-worn illumination device and the telemetry data from the casualty-worn informatics system, if available, are received by server 710 and passed to application(s) 714 via API 712. Application(s) 714 begin recording and storing the audio/video information and/or telemetry data to data store 716 for archival and training purposes. In addition, Application(s) 714 provide a feed of the audio/video information and telemetry data to one or more of the client stations 705a-705m, where it can be viewed by persons manning those stations.

Often, other medics, physicians, and emergency personnel will be the ones manning the client stations. As such, they have a direct audio/video link with the on-scene medic and can engage with that individual as he/she works on the casualty. For example, client stations may be equipped with one or more displays on which the video information from the medic's illumination device is displayed. So too may the telemetry data from the casualty-worn informatics system be displayed. And, the audio information from the medic-worn illumination device may be played over associated speakers or other audio output device (e.g., headphones) at the client station. The client station is also equipped with a microphone to allow the person manning the station to speak to the on-scene medic. Such audio transmissions are passed via the remote station 708 to the medic-worn illumination device and played over earpiece 28. In addition, if the medic-worn illumination device includes HUD projection optics 22, the person manning the client station may cause information concerning the casualty to be projected on a HUD screen disposed in front of the medic's eye(s). This can allow for playing of instructions, augmented reality views, etc. in aid of the on-scene medic's tasks.

The person manning the client station also may relieve the on-scene medic of tasks related to recording of the incident, notifying receiving hospitals or other care units, coordinating transport for the casualty, etc. If GPS or other location information is included in the information passed to the client station, the person manning that station can be provided displays of relative positions of the medic and casualty and any support units, thereby to coordinate an extraction of the casualty. Alternatively, or in addition, the medic may participate in such activities via mobile ad hoc networks established between various medic-worn illumination device.

By providing the facilities of a remote station with access to the on-scene medic's view of a casualty situation, on-scene care that is provided to the casualty may improve over that which is possible today. For example, a physician or other specialist may be able to view the condition of the casualty through the video provided via the medic-worn illumination device and offer the medic specific instructions for treating the casualty. Also, the recorded and stored information from the trauma scene may be later replayed during training or after-action sessions to allow others to learn from the incident and thereby affect how future trauma scenes are handled.

In one embodiment of the invention, the client stations of the remote system are not manned around the clock, but instead on an as-needed basis. For example, the client stations may be laptop or desktop computer systems possessed by off-duty personnel at their residences. In the event of a casualty situation, one of these individuals may be altered to the need to render assistance to an on-scene medic and then log-in to remote station 708 to engage with the on-scene medic as back-up support. He or she would then perform some or all of the tasks identified above.

Thus, a trauma scene monitoring system that integrates medic-worn appliances, patient-worn monitoring sensors, and a remote station where telemetry from each of these devices can be viewed, assessed, and acted upon in support of a field medic's first aid actions has been described.

What is claimed is:

1. A trauma scene monitoring system, comprising:
a medic-worn illumination device having a frame with one or more booms configured to position one or more light sources of the illumination device below a wearer's eyes near the wearer's zygomatic bones when the illumination device is worn on the wearer's head and to orient said light sources to project light in a direction of the wearer's view, audio/video means to capture audio/video data from a scene attended by the wearer, and a telemetry unit to a remote monitoring station;
a casualty-worn informatics system integrated within a band configured to be worn by a monitored individual, the informatics system including one or more sensors to provide the monitored individual's vital statistics and a telemetry unit configured to transmit data concerning said monitored individual's vital statistics to the remote monitoring station; and
the remote monitoring station having one or more receiving and presentation stations configured to receive and display the data concerning said monitored individual's vital statistics from the casualty-worn informatics system and the audio/video data from the medic-worn illumination device.

2. The trauma scene monitoring system of claim 1, wherein the one or more light sources of the medic-worn illumination device comprise light emitting diodes (LEDs) included in respective panels swivelly mounted to the one or more booms, and the audio/video means includes a video camera integrated in one of the panels.

3. The trauma scene monitoring system of claim 2, wherein the audio/video means of the medic-worn illumination device further includes one or both of a microphone and an earpiece.

4. The trauma scene monitoring system of claim 2, wherein the audio/video means of the medic-worn illumination device further includes bone conduction transducers for transmission and/or reception of audio signals.

5. The trauma scene monitoring system of claim 2, wherein the audio/video means of the medic-worn illumination device further includes a projector integrated in one of the panels.

6. The trauma scene monitoring system of claim 1, wherein the casualty-worn informatics system is integrated within a helmet retention system having a dial tensioning mechanism and which is adapted to be removably secured to a helmet.

7. The informatics system of claim 3, wherein the sensors of the casualty-worn informatics system include one or more sensor pads configured to contact the monitored individual at one or more points on the monitored individual's body, the sensor pads coupled to provide electrical signal inputs to a processor of the casualty-worn informatics system, which processor is configured to sample the signals from the sensor pads periodically and to transmit a record of the sampled signals to the remote monitoring station via the telemetry unit of the casualty-worn informatics system.

8. The informatics system of claim 7, wherein said processor of the casualty-worn informatics system is further configured to store a record of the sampled signals from the sensor pads in a writable memory of the casualty-worn informatics system, and the casualty-worn informatics system is further configured with an indicator to display a condition of the monitored individual's vital statistics.

9. A method, comprising:
   illuminating a scene using one or more light sources of an illumination device worn on a person attending a scene, the one or more light sources positioned on respective panels swivelly mounted to one or more booms of the illumination device and below the person's eyes near the person's zygomatic bones such that the scene is illuminated from a perspective and direction of the person's view of the scene;
   transmitting from a telemetry unit of the illumination device audio/video data captured by audio/video means of the illumination device, the transmitted audio/video data associated with a unique identifier of the illumination device;
   transmitting by a telemetry unit of a casualty-worn informatics system integrated within a band worn by a monitored individual at the scene data concerning said monitored individual's vital statistics captured by one or more sensors of the casualty-worn informatics system; and
   receiving and displaying at a remote monitoring station having one or more receiving and presentation stations configured the data concerning said monitored individual's vital statistics from the casualty-worn informatics system and the audio/video data from the medic-worn illumination device.

10. The method of claim 9, further comprising transmitting information from the remote monitoring station to the illumination device and presenting the information on a screen of the illumination device for view by the person.

* * * * *